United States Patent [19]

Reynolds

[11] Patent Number: 5,137,511
[45] Date of Patent: Aug. 11, 1992

[54] SYRINGE

[75] Inventor: David L. Reynolds, Montreal, Canada

[73] Assignee: Duoject Medical Systems Inc., Lac Brome, Canada

[21] Appl. No.: 437,203

[22] Filed: Nov. 16, 1989

Related U.S. Application Data

[63] Continuation-in-part of Ser. No. 72,015, Jul. 8, 1987, Pat. No. 4,886,495.

[51] Int. Cl.⁵ .............................................. A61M 5/00
[52] U.S. Cl. ...................................... 604/88; 604/416; 604/413; 604/191
[58] Field of Search ................. 604/82, 87, 88, 89, 604/91, 92, 191, 200, 201, 413, 414, 416

[56] References Cited

U.S. PATENT DOCUMENTS

| 2,542,814 | 2/1951 | Hoskins | 604/234 |
|---|---|---|---|
| 2,684,068 | 7/1954 | Orens . | |
| 2,728,341 | 12/1955 | Roehr . | |
| 2,828,743 | 4/1958 | Ashkenaz et al. . | |
| 2,832,340 | 4/1958 | Dann et al. | 604/228 |
| 2,842,126 | 7/1958 | Brown . | |
| 2,842,128 | 7/1958 | Hein, Jr. | 604/227 |
| 2,895,474 | 7/1959 | Reznek | 604/228 |
| 3,128,765 | 4/1964 | Tint | 604/228 |

(List continued on next page.)

FOREIGN PATENT DOCUMENTS

| 1766151 | 6/1971 | Fed. Rep. of Germany . |
|---|---|---|
| 632166 | 9/1982 | Switzerland . |
| 724671 | 2/1955 | United Kingdom . |
| 1030861 | 5/1966 | United Kingdom . |
| 1122787 | 8/1968 | United Kingdom . |
| 1252306 | 11/1971 | United Kingdom . |
| 1444119 | 7/1976 | United Kingdom . |
| 1496292 | 12/1977 | United Kingdom . |
| 1525455 | 9/1978 | United Kingdom . |

OTHER PUBLICATIONS

'Duocell Disposable Glass Syringe', International Medication Systems Limited (date unknown).
Catalog Page Showing 'Urojet', 'Puls-A-Jet' and 'Mini-Mix' Systems (date unknown).
'Vetter Lyo-Jet' Brochure, Vetter 1985.
"The Syringe-Phial 'Speed'", Steri Medical Supplies S.R.L. (date unknown).
'Kimble Glass Capabilities' brochure (date unknown).
'West Capabilities . . . Glass Products' brochure (date unknown).

Primary Examiner—Stephen C. Pellegrino
Assistant Examiner—Ralph A. Lewis

[57] ABSTRACT

A prefilled syringe for one or two component medicaments is based upon the use of a vial containing a medicament or one component of a medicament, the vial having an open bottom closed by a piston. When a flexible extension of the piston is coupled with a tubular plunger, and an adaptor cap having an internal needle and an external connection for a needle is placed over a cap of the vial, the latter is converted into a prefilled syringe. The piston may have an axial passage closed by a resealable septum, so that a separate diluent stored in a flexible capsule may be introduced into the vial through the piston by a double ended needle mounted on a further cap applied to the capsule, the further cap being coupled within the tubular interior of the plunger so that the double ended needle penetrates the septum in the piston. The capsule is pushed forward onto the double ended needle when its contents are to be expelled into the vial. The capsule and its cap are then removed and discarded. In an alternative arrangement, the cap of the capsule is coupled to the adaptor cap and the diluent introduced into the vial through a closure secured by the cap of the vial, after which the capsule is removed from the plunger and the latter is coupled to the piston.

11 Claims, 8 Drawing Sheets

U.S. PATENT DOCUMENTS

| | | |
|---|---|---|
| 3,150,661 | 9/1964 | Maki . |
| 3,437,090 | 4/1969 | Sarnoff . |
| 3,489,147 | 1/1970 | Shaw . |
| 3,542,240 | 11/1970 | Solowey . |
| 3,547,122 | 12/1970 | Rinser . |
| 3,563,373 | 2/1971 | Paulson . |
| 3,570,486 | 3/1971 | Engelsher . |
| 3,636,950 | 1/1972 | Gomez et al. . |
| 3,678,931 | 7/1972 | Cohen . |
| 3,682,174 | 8/1972 | Cohen . |
| 3,724,460 | 4/1973 | Gomez et al. . |
| 3,785,379 | 1/1974 | Cohen . |
| 3,845,763 | 11/1974 | Cloyd . |
| 3,872,867 | 3/1975 | Killinger . |
| 3,903,886 | 9/1975 | Omotani . |
| 3,923,059 | 12/1975 | Ogle . |
| 3,994,296 | 11/1976 | Cloyd . |
| 4,014,330 | 3/1977 | Genese . |
| 4,055,177 | 10/1977 | Cohen . |
| 4,059,109 | 11/1977 | Tischlinger . |
| 4,060,082 | 11/1977 | Lindberg et al. . |
| 4,112,945 | 9/1978 | Helixon et al. ................ 604/232 |
| 4,171,698 | 10/1979 | Genese . |
| 4,180,070 | 12/1979 | Genese . |
| 4,390,016 | 6/1983 | Riess . |
| 4,568,336 | 2/1986 | Cooper . |
| 4,581,016 | 4/1986 | Gettig . |
| 4,583,971 | 4/1986 | Bocquet et al. ................ 604/414 |
| 4,675,020 | 6/1987 | McPhee ........................ 604/414 |
| 4,723,956 | 2/1988 | Schnell et al. ................ 604/408 |
| 4,731,068 | 3/1988 | Hesse . |
| 4,755,169 | 7/1988 | Sarnoff et al. . |
| 4,861,335 | 8/1989 | Reynolds ........................ 604/191 |
| 4,886,495 | 12/1989 | Reynolds . |
| 4,931,043 | 6/1990 | Ray et al. ........................ 604/228 |

SYRINGE

BACKGROUND OF THE INVENTION

This application is a continuation in part of Ser. No. 072,015 filed Jul. 8, 1987 now U.S. Pat. No. 4,886,495.

FIELD OF THE INVENTION

This invention relates to prefilled syringes for use in medical or veterinary treatment.

REVIEW OF THE ART

There has been an increasing trend in recent years to the putting up of pharmaceuticals in dosage forms so as to minimize the preparation required to administer a medicament to a patient and to reduce the chances of dosage errors or contamination. One dosage form which has been gaining rapid acceptance is the prefilled disposable syringe. Various difficulties are however associated with the preparation and usage of such syringes, particularly in the case of preparations which, in ready to use condition, have a short shelf life. Numerous forms of dual compartment syringe structures have been proposed for the shipping of such preparations with components stored in separate compartments for admixture immediately prior to use. Although certain structures have met with some degree of acceptance, they are commonly difficult to manufacture and/or use because of difficulties in filling the syringe with the components, and because they require extensive manipulation immediately prior to use. Moreover they are frequently substantially more bulky than conventional syringes because in many cases they frequently comprise components which effectively represent two syringes in tandem.

Problems in the manufacture of prefilled syringes are not confined to two component systems and even with single component systems the filling of syringes under factory conditions is difficult to mechanize effectively and requires expensive special purpose syringe filling machinery. The same applies to related units prefilled with liquids required for injection or infusion during medical procedures.

Another approach where single component systems are involved is exemplified by British Patent Specifications Nos. 1,252,306 and 1,444,119, and U.S. Pat. No. 4,445,895, in which a prefilled cartridge having a displaceable plug at one end, and a needle penetrable closure at an opposite end, is inserted into the barrel of a syringe for dispensing of its contents. Whilst such cartridges and the equipment for filling them are known and available, they are only really suitable for preparations which can be stored in liquid form, and require either a special or a modified syringe for their use. The cartridges themselves require special filling apparatus.

In a further arrangement disclosed in U.S. Pat. No. 3,845,763, a cartridge or vial is closed at its bottom end by a slidable plug with a downwardly extending stem, which cartridge or vial is inserted bottom end first into a special holder which carries a double ended needle, so that the stem is penetrated by the needle and the body of the vial is converted into a plunger which can be depressed to expel the contents of the vial through the stem. The projecting stem means that the vial cannot be filled utilizing conventional vial filling machinery.

The high capital expenditure involved in implementing known prefilled syringe systems has severely limited their adoption to those few cases where their advantages outweigh the substantial additional unit costs involved as compared to conventional modes of delivery.

SUMMARY OF THE INVENTION

The present invention seeks to provide a system for the distribution of preparations required for injection or infusion in liquid dosage form during medical procedures, which has a wide range of utility both for single component liquid preparations or for two component systems of which one component may be a solid, which utilizes a small number of components all suitable for mass production using material already approved for usage in such applications, and which is simple to assemble and can be filled utilizing equipment already available to most pharmaceutical manufacturers.

The system is based upon and built around a basic component in the form of a 'bottomless vial'. Such a bottomless vial has all of the characteristics of a conventional pharmaceutical vial, except that the glass base of the vial is replaced by a piston wholly received within the vial and designed to form a hermetic seal with its cylindrical side wall, the seal being maintained both when coupled and when uncoupled from a plunger releasably connectable to the piston for moving the latter axially of the vial. A particularly important characteristic of such a bottomless vial is that it can be conveyed, filled and capped reliably by conventional vial filling and handling equipment such as is already possessed by most pharmaceutical manufacturers. To this end, the bottomless vial must be free of features which would significantly compromise its stability when handled by such equipment. Thus any flange around the base of the vial must result in no more than a slight increase in the overall diameter of the vial, so as to avoid any substantial increase in its tendency to tip when jostled by other similar vials, and the center of gravity of the vial must not be displaced so far upwardly as to substantially reduce the stability of the vial.

The piston must be capable of maintaining a hermetic seal with the wall of the vial of integrity comparable to that achieved during capping of a conventional vial, and this seal should be maintained during manipulation of a syringe system incorporating the vial, during which the piston may be subject to non-axial forces transmitted to it by a plunger and tending to break the seal.

In the context of the invention, it should be understood that "vial" refers to a particular type of container, having a rather squat cylindrical body whose height compared to the diameter of its base is such that it may stand stably on its base whilst being conveyed through a vial filling machine and subsequently sealed and capped. Its body should also be free of external projections large enough to interact with other vials or the filling machinery in a manner such as to promote tipping. A vial has a neck with a large enough internal diameter to permit filling from a vial filling machine: solid filling materials will normally require a larger neck than liquids. Vials should not be confused with cartridges, which are comparatively long and slim, and cannot usually be filled utilizing vial filling machinery since they are too tall to rest in a stable manner on their bases.

Accordingly the present invention provides a vial formed of rigid transparent material and consisting of a cylindrical body, said body having an open bottom end having an external diameter at most only slightly greater than that of the remainder of the body, but sufficient relative to the height and center of gravity of the vial as a whole to support the latter in a stable manner when conveyed standing on its open end through vial filling and capping machinery, injectable material within the body, a comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlaying the closure to secure the closure to the neck with the closure presenting a needle penetrable central portion, an impervious substantially solid piston of resilient material sealingly received within said body at its lower end beneath said injectable material and above said open bottom end, and an extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap.

The differences between such a vial and a conventional vial do not prevent it from being filled and capped in conventional vial filling and capping machinery; indeed, apart from the replacement of the bottom wall of the vial by a piston as specified, it is a conventional vial, and can be handled normally by the machinery during filling with either liquid or solid material. The presence of the piston which is relatively massive, in the lower part of the vial even helps stabilize the latter during filling. Furthermore, liquid filled vials may be lyophilized utilizing special stoppers either as known in the art or as described below. Obviously the cubic capacity of such a vial is less than the capacity of a conventional vial of comparable overall dimensions but for most purposes this is immaterial.

A vial in accordance with the invention may be converted into a syringe by the addition of a plunger coupled to the piston and an outer cap which acts as a needle carrier. More specifically, the syringe includes as well as the vial a syringe plunger connected to the flexible extension from the piston, and an outer cap engaged over the cap of the vial, the outer cap having a hollow needle projecting axially within the cap and a coupling for engagement with injection means and communicating with said hollow needle, the outer cap being axially movable relative to said cap of the vial from a position in which the needle ends short of the cap of the vial to a position in which it penetrates the cap of the vial. The plunger is provided with radially extending flanges for sustaining actuating forces applied to the syringe through a flange grip provided on the outer cap or on a plunger guide or piston stabilizer ring applied to the open end of the vial.

In a syringe for a two component medicament, it is necessary to provide for packaging of the second component and its admixture with the first component in the vial prior to dispensing. The invention thus further extends to a capsule assembly comprising a generally cylindrical sealed capsule having walls formed of a flexible needle penetrable material of suitable properties, a generally cylindrical neck defined by said walls at one end of the capsule, said neck having axially spaced inner and outer peripheral ridges, and a generally cylindrical cap applied to said neck so that a detent within the cap engages the outer peripheral ridge on the neck, a hollow cannula being formed integral with and passing through said cap so that an inner penetrating end within the cap ends short of the neck of the capsule and an outer end formed either in the form of a needle or a fluid coupling which extends outwardly of the cap, the cap being displaceable relative to the capsule to a position in which the detent rides over the inner ridge and the inner end of the needle penetrates the neck of the capsule, the cap and capsule being of a diameter such that they can enter the tubular plunger to a position in which the outer end of the cannula, if of needle form penetrates the septum of the piston when the plunger is engaged with the latter. An alternative arrangement may be used where the outer end of the cannula is a coupling, in which case the latter is connected to the coupling on the outer cap of the syringe, with the plunger being used as a support for the capsule prior to being coupled to the piston.

Thus the injection system comprises a sequence of components of which various sub-sequences can be combined to form injection systems for preparations requiring shipping and storage as two separate components, certain sub-sequences themselves having utility respectively as injection systems for single component liquid preparations. "Injection" is utilized broadly to cover hypodermic, intramuscular and intravenous injection, gravity and mechanical infusion, and injection into other vessels utilized in medical treatment or testing. For the purposes of description, the "front" or "top" end of an injection system will be considered the end of the system from which a liquid preparation is so injected.

The arrangement including the capsule assembly has a number of advantages in the manufacture and use of prefilled syringes for two component systems; furthermore, without the third cap and the sealed capsule containing the second component the remaining components provide, according to a further feature of the invention, advantages in the manufacture and use of prefilled syringes for single component systems. The third cap and sealed capsule provide, according to yet a further feature of the invention, an advantageous subsystem for various applications in which a sealed sterile source of a liquid is required for injection, or dropwise introduction into other containers used in medical procedures. With prefilled syringes for two components systems, either the capsule or the capsule and the third cap, may be sold, or shipped separately. This enables different diluents or sizes of capsule to be selected, or a common set of diluent capsules to be utilized with syringe assemblies containing different first components, thus simplifying inventory control.

Further features of the invention will become apparent from the following description of a preferred embodiment thereof with reference to the accompanying drawings.

DESCRIPTION OF THE PREFERRED EMBODIMENT

Figure 1:
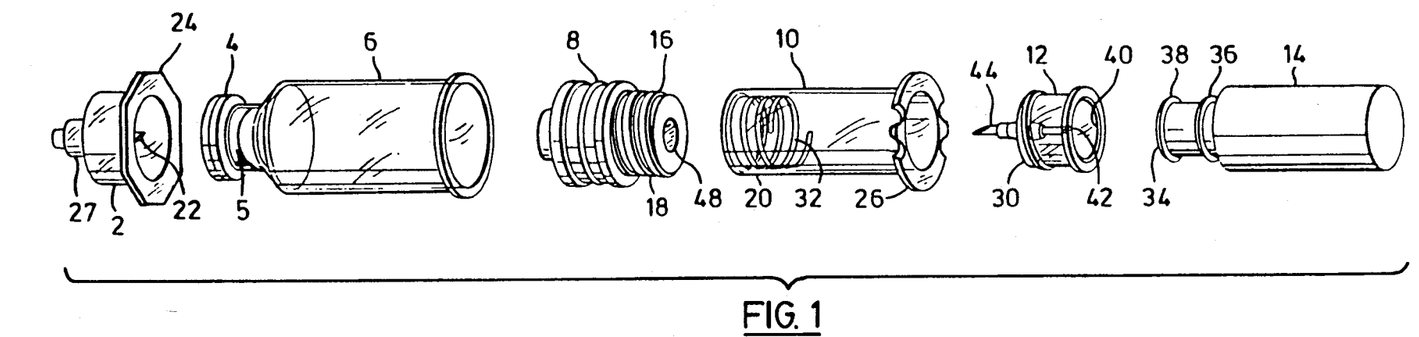
FIG. 1 is a perspective exploded view of the mechanical components of a syringe system including a vial in accordance with the invention.
Figure 2:
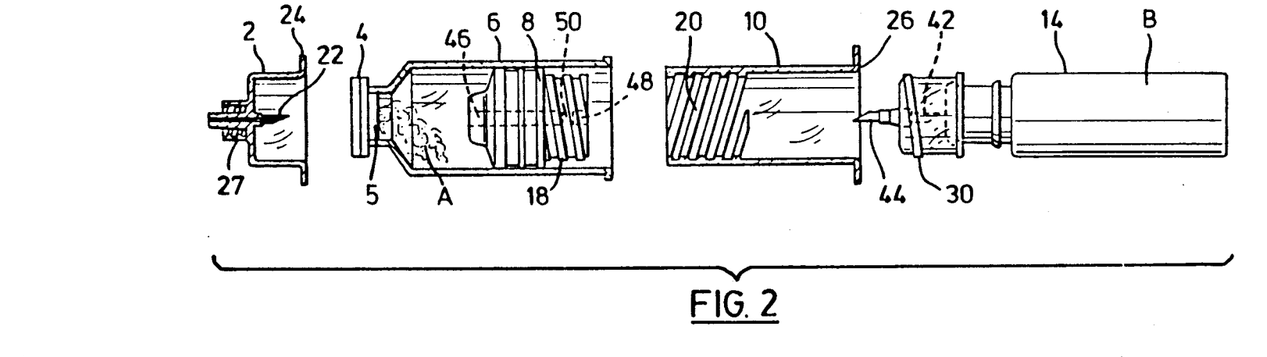
FIG. 2 is a partially longitudinally sectioned, partially exploded view of the syringe components showing some further details of their construction.

Referring to FIGS. 1 and 2, a syringe system for the injection of a liquid preparation stored as two components comprises seven primary mechanical components, apart from the components of the preparation, which latter are shown in FIG. 2 but not FIG. 1. The components of the preparation typically comprise a first component A which may be in any physical state suitable for storage in vial, and a second liquid component B, typically but not necessarily sterile water. The liquid component B is stored in a sealed capsule 14 of flexible material, manufactured using conventional techniques from a material, usually synthetic plastic, which is compatible with the contents of the capsule. The first component is stored in a cylindrical vial 6, typically of glass, and capped by an annular cap 4 which retains a conventional needle penetrable sealing member accessible through a central opening in the cap. By a vial is meant a cylindrical vessel which can assume a stable upright position supported by its base, the overall height of the vessel preferably not exceeding 2.5 times the external diameter of the rim of its base so that it remains stable when passing through conventional vial filling and capping equipment utilized to fill and cap the vial. A neck at the upper end of the vial 6, which is capped by the cap 4, has a relatively internal diameter characteristic of such vessels, usually not less than about 7.5 mm for liquid or 10 mm for solids, so that filling either liquids or solids can be readily achieved. The cap 4 is formed by an aluminum sleeve, having a flange retaining a sealing member formed by a soft rubber disc or plug 5 over or in the front end opening, and tightly crimped onto a neck at the front end of the vial so as to seal the latter. A major difference from conventional vials is that the conventional bottom wall of the vial is replaced by an axially movable piston 8 wholly within the vial and in sealing contact with the vial walls. When received within the vial 6, this piston in no way interferes with the handling of the vial using conventional machinery, and in particular permits the vial to be stood on its base with its neck (which forms the front end of the vial when in use) upwards as it passes through the filling and capping equipment.

Figures 6, 7, 8:
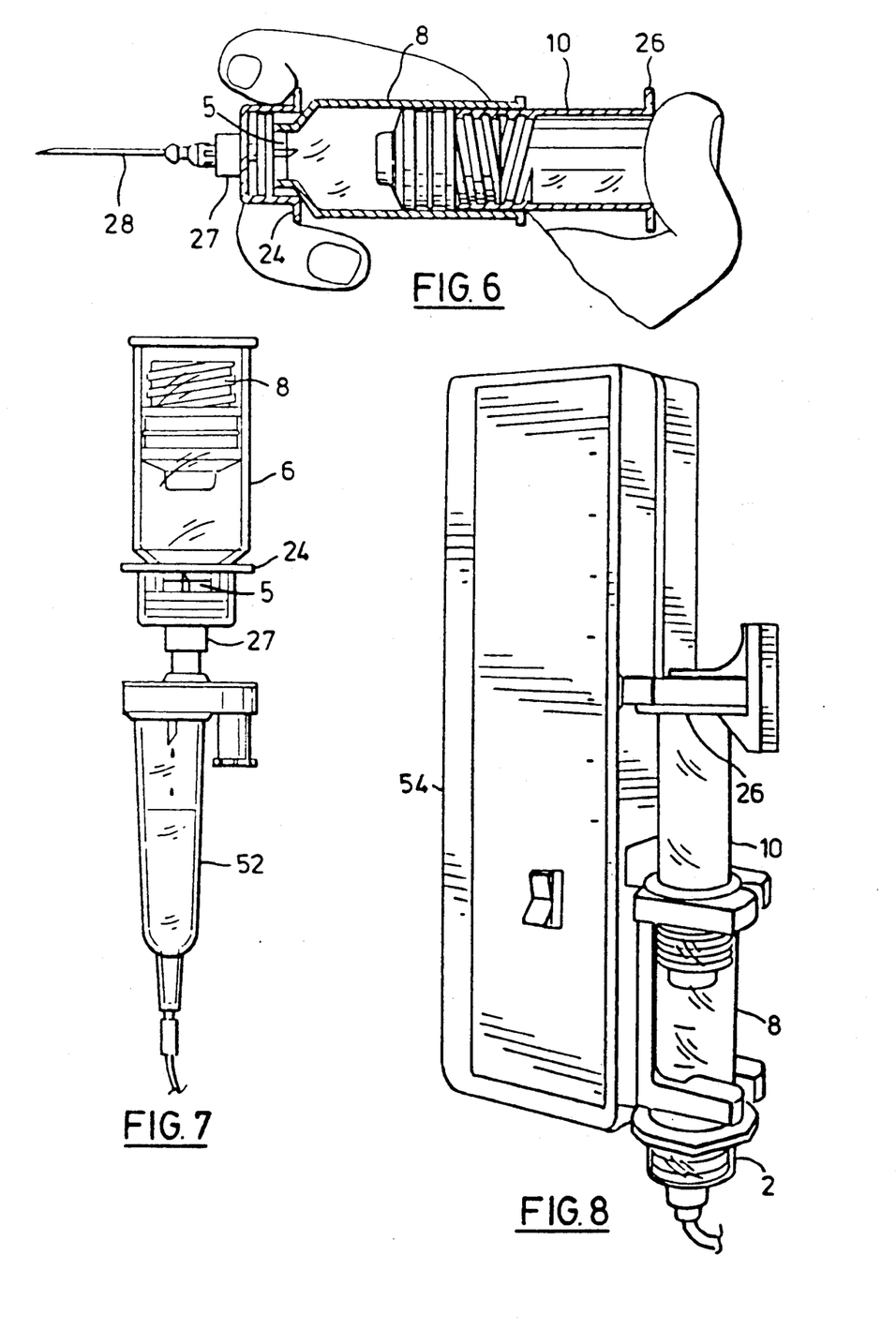
FIGS. 6, 7 and 8 illustrate exemplary applications of the syringe.

The filled vial 6 may be converted into a prefilled syringe by applying an outer cap 2 over the cap 4 and positively attaching a cylindrical plunger sleeve 10 to the piston 8. The piston 8, typically formed of rubber, is moulded with a rearward extension 16 with an external thread 18, whilst the interior of the front end of the plunger sleeve 10 is formed with a complementary internal thread 20 so that it may be screwed onto the piston 8. The outer cap 2 fits over the inner cap 4 so that a hollow needle 22 formed within the cap 2 does not reach the penetrable zone of the cap 4. On the front of the cap 2 and in communication with the hollow needle 2 is a coupling adapter 27, for example similar to those sold under the trade mark LUER-LOK, for connection of the syringe to a needle 28 or other instrumentality (see FIGS. 6–8). To prepare the syringe for use, the outer cap 2 is pulled back over the inner cap 4 so that the needle 22 penetrates the cap, and the needle 28 or other instrumentality is applied. This should be done without pressing on the plunger sleeve so as to avoid accidental ejection of the contents of the syringe. The rear ends of both cap 2 and the sleeve 10 are formed with radially extending flanges 24 and 26 respectively which form finger grips for operation of the syringe. Thus if a user grips the syringe by the flanges as shown in FIG. 6 and presses them towards each other, the contents of the syringe can be expelled through the needle 22 and the needle 28. It will be noted that the rear end of the vial 6 is formed with only a relatively slight external bead 7 rather than the wide finger flange commonly found on the barrels of conventional syringes. In the present arrangement, the flange 24 provides the function of such a finger flange, enabling the bead 7 to be reduced to a size which will avoid such interference between the flanges of adjacent vials as would cause tipping when the vials are conveyed in a vertical attitude through filling and capping equipment.

In many applications, it is desirable to prevent premature penetration of the plug 5 by the needle 22, and therefore the cap 2 may be moulded with short internal threads (not shown) which prevent rearward movement of the cap 2 unless it is twisted so that the threads bite into the soft aluminum of the cap 4 and draw the cap 2 rearwardly so that the needle 22 can penetrate the plug.

A prefilled syringe constructed as discussed above has significant advantages over conventional prefilled syringes in that the vial may be filled using conventional vial filling equipment, and yet may be utilized directly instead of requiring its contents to be transferred to a syringe prior to use as has been conventional in the use of vials.

The vial may also be charged with material which is not directly injectable, such as solids which must be dissolved or suspended in a liquid medium prior to injection. In this case the liquid medium is sealed as already described in a flexible capsule 14. A third cap 12 is either applied to the capsule as shown in FIG. 2, or inserted into the plunger sleeve 10 so that a screw thread 30 on the exterior of the cap engages the screw thread 20 within the sleeve.

A neck 34 of the capsule 14 has two peripheral ridges 36 and 38. If the cap 12 is applied to the capsule, a detent 40 within the cap is pushed over only the outer ridge 38 so that a rear end portion 42 of a hollow needle mounted in the cap stops short of the end of the capsule. By forcing the detent 40 rearwardly over the ridge 36, the needle portion 42 can be forced rearwardly so as to penetrate the capsule. A forward end portion 44 of the hollow needle has a length such that when the cap 12 is screwed into the sleeve 10, and the sleeve 10 is screwed onto the piston 8, the needle portion 44 penetrates a resilient septum 50 normally separating axial passages 46 and 48 formed in the front and rear of the piston.

Figure 3:
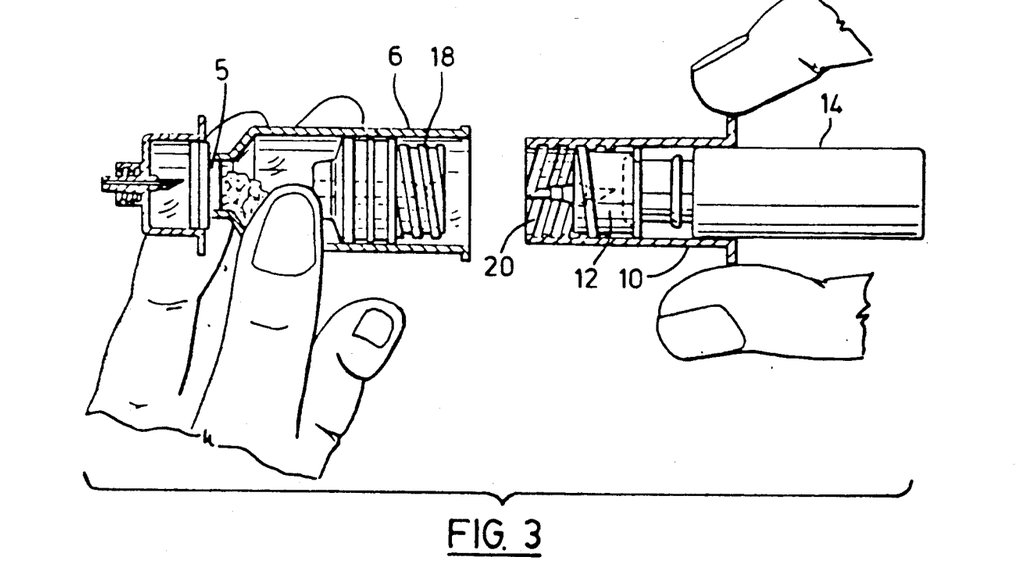
FIGS. 3, 4 and 5 illustrate preparation of the syringe system to provide a syringe ready for use.
Figure 4:
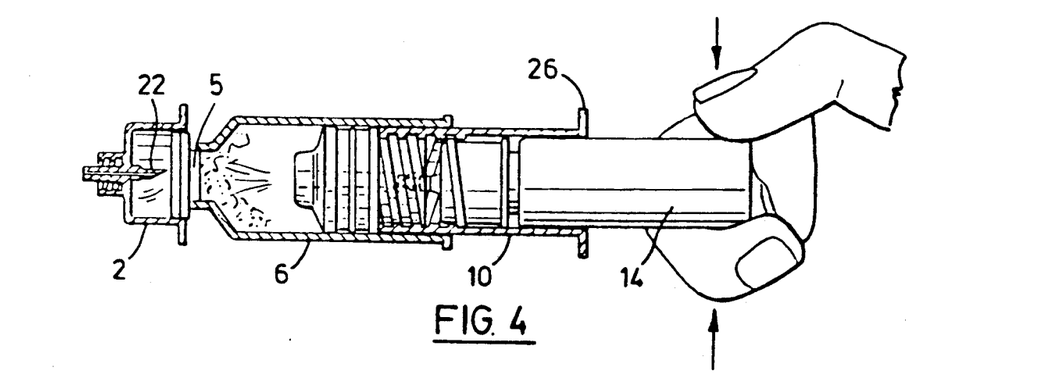
Figure 5:
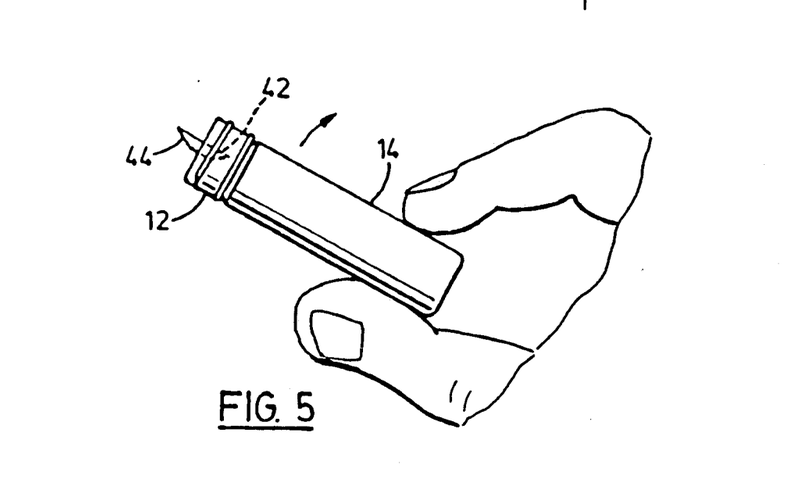

In use, if the capsule 14 and cap 12 are shipped as a separate unit, this unit is screwed into the sleeve 10 (see FIG. 3), and the sleeve 10 is pushed into the rear of the vial 6 so that the needle portion 44 penetrates the septum 50 of the piston 8 and the thread 20 is screwed onto the thread 18 of the piston (see FIG. 4). This action also substantially unscrews the cap 12 from the thread 20. The capsule 14 is then pressed forward onto the needle portion 42, and the liquid contents of the capsule can then be squeezed through the needle and into admixture with the first component in front of the piston 8. Thereafter the capsule 14 and cap 12 may be pulled as a unit from the sleeve 10 and discarded (see FIG. 5). The septum 50 reseals as the needle portion 44 is withdrawn, leaving a syringe ready for use as illustrated in FIGS. 6-8. Alternatively, if the cap 12 is prefitted to the sleeve, the sleeve 10 may be screwed onto the piston 8, and the capsule 14 pressed into the sleeve 10 and the cap 12 so as to establish communication between the capsule and the space forward of the piston, the procedure thereafter being the same.

Rather than being used conventionally with a needle as shown in FIG. 6, the prepared syringe may be used for gravitational or mechanical infusion as shown in FIGS. 7 and 8. In FIG. 7, the adapter 27 is fitted to a complementary coupling on a gravity infuser 52 to provide a drip feed, the sleeve 10 having been unscrewed and discarded, together with the cap 12 and capsule 14, if used. In FIG. 8, the syringe is mounted in a mechanical infuser 54 such as that sold under the trade mark BARD, the latter being equipped with clamps 56, 58, 60 suited for engagement with the syringe.

By basing the system on an open-bottomed vial 6 closed at its bottom end by a piston 8 equipped with means such as the screw thread 18 for coupling it to a plunger of sleeve form, and with a needle penetrable septum 50, in optional conjunction with sealed flexible capsules of diluent, great flexibility in application can be obtained, using components which are easy to fill, compact to ship, and easy to make ready for use.

Figure 9:
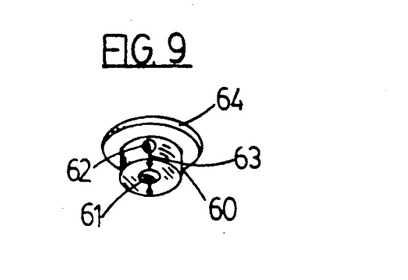
FIGS. 9 and 10 illustrate an optional feature of a vial in accordance with the invention.
Figure 10:
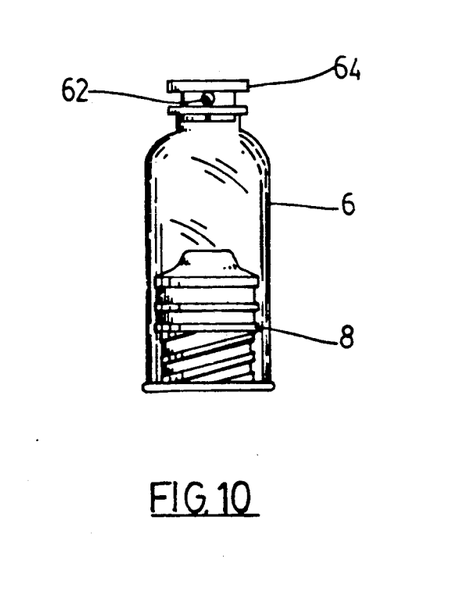

Referring now to FIGS. 9 and 10, the rubber disk or plug retained by the cap 4 on the vial 6 may be replaced by a modified plug 60 as shown in perspective from beneath and one side in FIG. 8, and partially installed on a vial 6 in FIG. 9. Use of such a plug 60 is advantageous when the solid component of a medicament is to be prepared in situ in the vial by lyophilization. The vial is filled with a liquid preparation to be lyophilized, and plug 60 inserted to the position shown in FIG. 9, so that the interior of the vial communicates with its environment through a central passageway 61 and radial bores 62, the passageway and the bores being no larger than needed for the removal of water vapour during lyophilization. The plug is split at 63 to facilitate moulding. After filling the contents of the vial are rapidly frozen and vacuum dried to leave a solid residue in the vial which can be reconstituted immediately before use. The plug 60 is then moved to the full extent permitted by a flange 64 into the neck of the vial 6 and secured by a cap 4. Whilst a conventional lyophilization stopper could be utilized in place of the plug 60, the latter has the advantage of minimizing the amount of liquid trapped within the stopper during use of the syringe. For the same reason, the head of the piston 8 is shaped so as to minimize dead space in the neck of the vial when the contents of the vial are expelled during use of the syringe.

Figure 11:
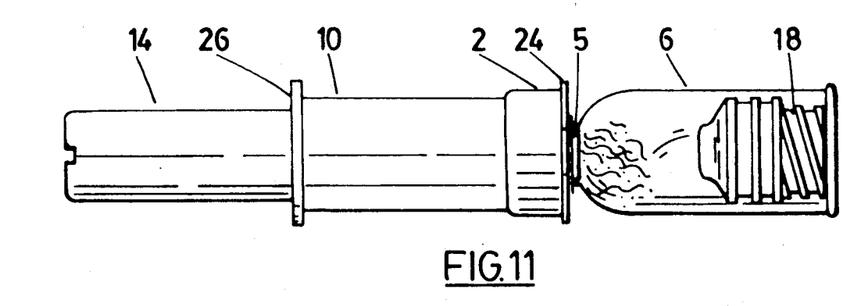
FIGS. 11 and 12 are elevational and exploded views of an alternative embodiment of the syringe system.
Figure 12:
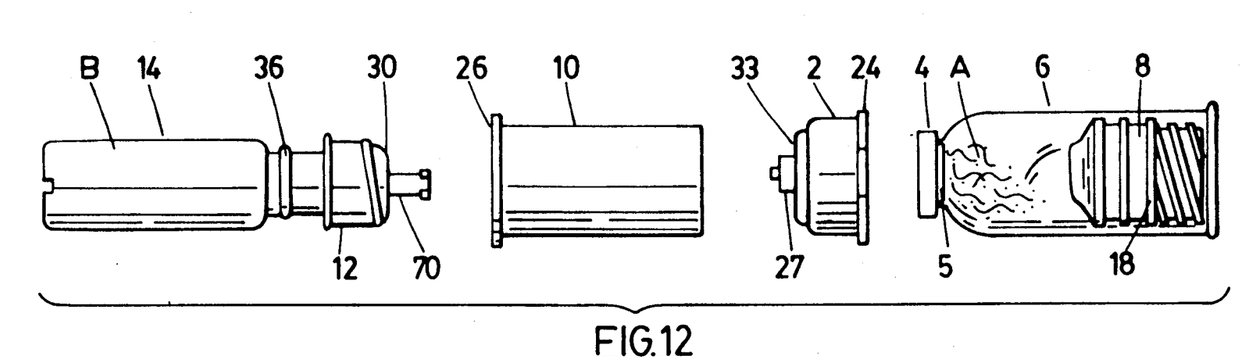

FIGS. 11 and 12 illustrate an alternate configuration of the syringe. The various components are essentially identical to those already described, and the same reference numerals are utilized except that the outer needle 44 of the conduit extending through the cap 12 is replaced by an extension 70 which is configured at its outer end to couple with a standard syringe coupling such as the coupling 27 on the cap 2. This enables the capsule 14, once inserted in the plunger 10, to be locked through the extension 70 and the coupling 27 to the cap 2 to produce the compact assembly shown in FIG. 11. The inner end of the plunger 10 is a press fit on an annular retaining flange 33 formed on the cap 2. To prepare the syringe for use, the cap 2 is forced rearwardly over the cap 4 so that the needle 22 (see FIG. 2) pierces the seal 5, and the capsule 14 is forced forward so that it is pierced by the needle 42 and its contents can be expelled through the needle 42, the extension 70, the coupling 27 and the needle 22 into the vial 6. The assembly of the capsule 14 and the plunger 10 can then be released from the remainder of the syringe by turning so as to release the extension 70 from the coupling 27, a needle (not shown) may be applied to the coupling 27, the capsule 14 is removed from the plunger 11 and discarded, and the plunger 11 is screwed onto the coupling 18 to ready the syringe for use. With this arrangement, the passage 46 in the piston 8 is not required, although the passage 48 may be retained to save material and enhance the flexibility of the extension 18 of the piston.

Figure 13:
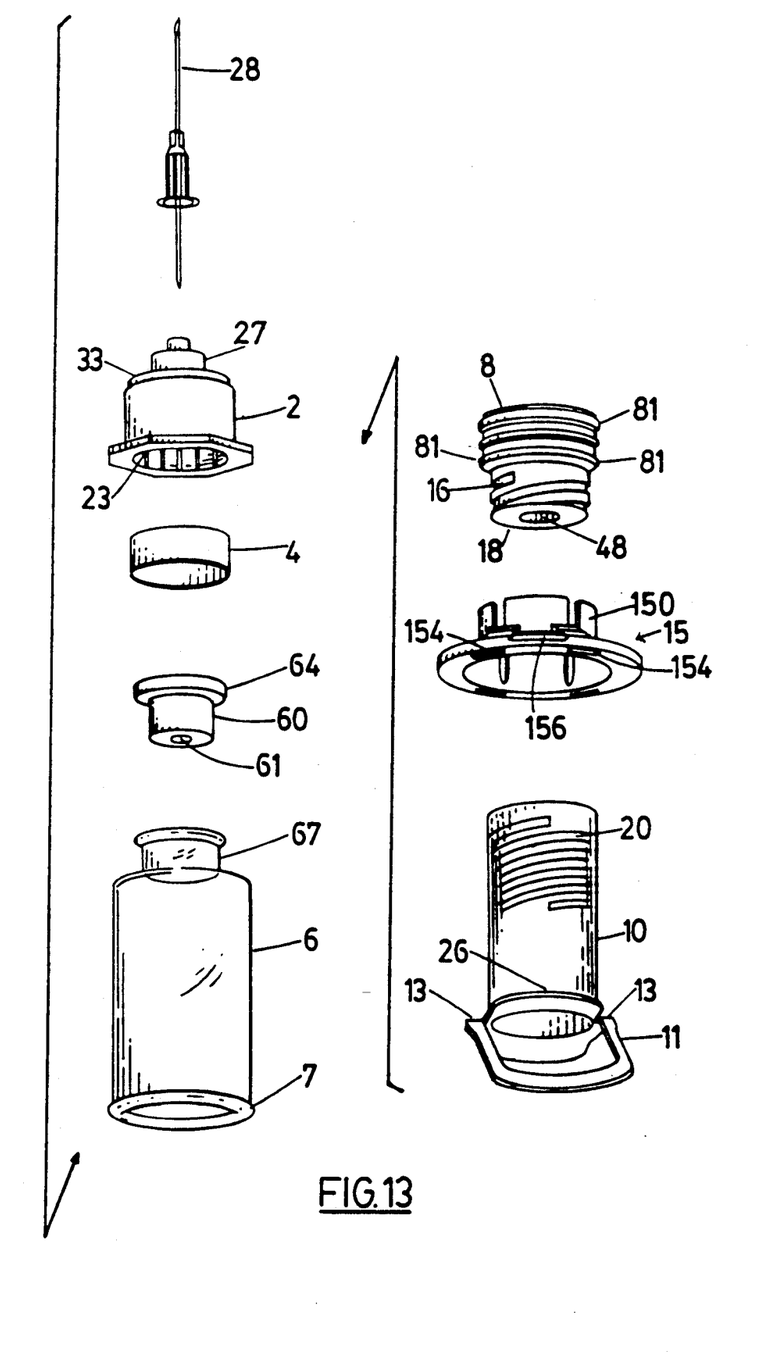
FIG. 13 shows the separated parts a further embodiment of the syringe system.
Figure 15:
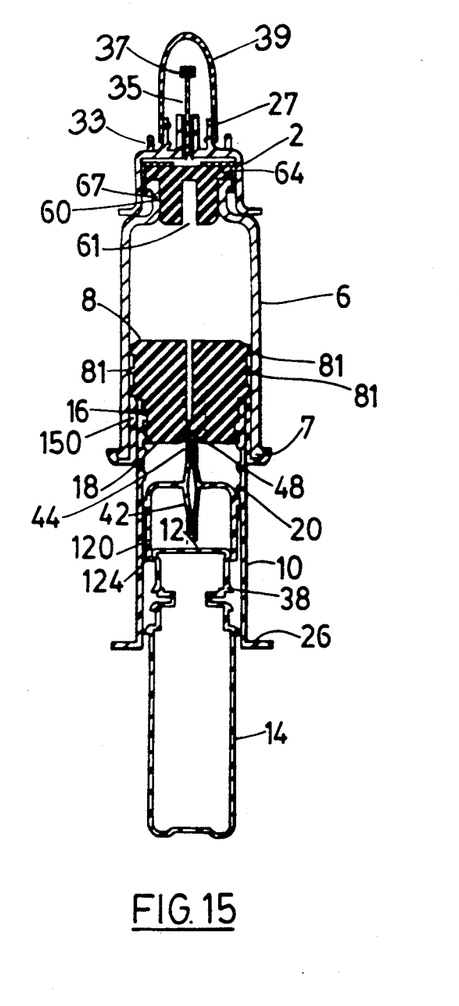
FIG. 15 is a longitudinal cross section through the assembled system of FIGS. 13 and 14.

A similar arrangement may be utilized for single component medicaments in which case the capsule 14 and cap 12 are not provided. The arrangement is advantageous for both single and multiple component medicaments since only the vial need be assembled and filled in a clean room, the only additional step required over the filling of a conventional vial being the insertion of the piston 8. The plunger 10 may be pressed onto the cap 2, and this assembly, if desired together with a needle and/or a capsule 12 and cap 14, may be separately sterilized and packaged, without endangering the stability or destroying the contents of the vial, which will often be sensitive to heat or radiation utilized for sterilization purposes. Since the capsule 12 can withstand conventional terminal sterilization techniques (see further below), it can be sterilized independently of the vial. This is a major advantage over many two-component syringe systems in which the components are separated only by some form of penetrable plug or diaphragm and must therefore either be fully assembled in a clean room, or subjected in assembled form to terminal sterilization techniques which may destroy or damage a component of the pharmaceutical preparation.

Where the capsule 12 is not being used, it is possible to utilize a cap 2 in which the needle 22 is not provided, and instead use a needle arrangement as shown in FIG. 13 or FIG. 15.

Figure 14:
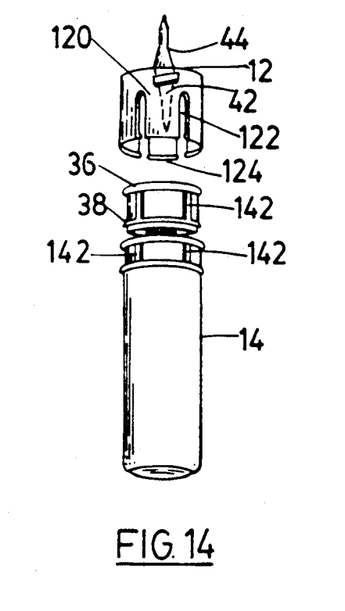
FIG. 14 shows, separated, a diluent capsule and cap for use with the system of FIG. 13.

Features of presently most preferred embodiments of the invention are shown in FIGS. 13-15. The same reference numerals are used to denote the same parts in these figures as in the previous embodiments, where applicable, and construction and operation are similar except where otherwise indicated.

FIG. 13-15 show a further vial and syringe system according to the invention, the vial comprising a body 6 of rigid transparent material, usually glass although synthetic plastic resins might be utilized in certain applications. The body has the general configuration of a conventional vial except for the absence of a bottom wall. In order to compensate for the strengthening effect which would be provided by the bottom wall, in order to provide a detent for an optional plunger stabilizer ring 15 described further below, and in order to permit a slight flare at the extreme bottom end of the vial, a rounded bead 7 is provided around the perimeter of the bottom end of the body, although its peripheral extent should not be sufficient to increase substantially the diameter of the vial or decrease substantially its stability during handling.

A medicament A is retained within the vial by a piston 8. A closure 60 substantially fills a neck portion 67 of the vial after the vial, closed at the bottom by the piston, has been filled through its neck portion by a conventional vial filling machine. Although the medicament shown in a solid, it may be a liquid, or filled as a liquid and lyophilized to leave a solid residue. The piston 8 is moulded from rubber, preferably of at least 50 durometer hardness, and is formed with multiple, preferable three, peripheral ribs 81 on its outer surface, the external diameter of the ribs being slightly greater than the internal diameter of the body 6 so that an hermetic seal is established when the piston is pressed into the bottom of the body, initial entry being assisted by the flare mentioned above. The piston is moulded as a substantially solid body so that it has sufficient rigidity to maintain the desired hermetic seal with the body, any central bores within the piston (see FIG. 15) required to assist needle penetration being of insufficient radial extent to have any significant effect on its rigidity. Although in the piston shown in FIG. 16, a central bore 48 does just extend into the piston proper, its axial extent within the piston and its diameter are sufficiently small relative to the piston diameter that the rigidity of the piston is not substantially reduced. The longer bore 46 through the piston shown in FIG. 15 is of even smaller diameter so as not to prejudice piston rigidity.

The piston has a downward extension 18 of reduced diameter, in which the bore 48 is also present. The diameter of the bore 48 forms in this case a greater portion of the diameter of the extension 18, whose flexibility is thus somewhat increased by its presence. The extension carries on its outer surface a multistart thread, defined by grooves 16 which terminate abruptly short of the piston, forming abutments serving a purpose discussed further below. Provided that the hardness and rigidity requirements for the piston as a whole are met, the rubber utilized to form the piston, and any external coating on the rubber (which may act to increase the effective hardness of the rubber), are selected for compatibility with the medicament contained in the syringe, a number of approved materials being available and well known in the pharmaceutical art.

The neck closure 60 may be formed of similar rubber, and is similar in construction to that shown in FIGS. 9 and 10 if lyophilization of the syringe contents is required: otherwise the slot 63 and bores 62 (see FIG. 9) may be omitted. After insertion of the closure 60, its flange 64 may be held in place by a conventional cap 4 crimped over the flange and a flange on the neck of the bottle. Such a cap 4 may have a flip-off top attached to a separable central portion of the cap, partially severed from the remainder of the cap so that these portions may be broken away prior to assembly of the syringe to expose a central needle penetrable zone of the closure 60 above the bore 61.

The piston together with its extension 18 is relatively massive, with a weight which typically amounts to at least a major portion of that of the body 6. This weight in the lower part of the body assists in stabilising the vial during handling and filling and further inhibits tipping.

As mentioned above, vial assembly and filling will normally be performed in a clean room, since many pharmaceuticals will not withstand terminal sterilization procedures. The only additional step which requires to be carried out in the clean room other than is conventional in the filling of vials is the insertion of the piston 8.

In order to convert the basic vial into a syringe system, either one of two different approaches can be used, similar respectively to those described with reference to FIGS. 1 to 6 and FIGS. 11 and 12 above. Only the differences from that corresponding to FIGS. 1 to 6 will be described in detail for the present embodiment, since the differences from the system of FIGS. 11 and 12 arrangement will in general be similar. FIGS. 13 and 14 show the components of a syringe system separated, whilst FIG. 15 shown them assembled and sectioned (although an alternative needle arrangement is shown in FIG. 15). It should be understood that the diluent cartridge 14 and cartridge cap 12 are optional features of the system and will only be utilized when a diluent or solvent is required for the content of the vial which is not provided by some other means. When building a system similar to that shown in FIGS. 11 and 12, the same parts will be used, except that if the cartridge 14 and the cap 12 are used, the cap 12 will be modified in the manner illustrated in FIGS. 11 and 12. Assembly in the manner described with reference to FIGS. 11 and 12 has the advantages already described.

Referring to FIGS. 13 and 15, an outer cap 2 is pushed over the cap 4, and is similar to that shown in FIGS. 1, 2 and 12, except that the internal needle 22 shown in FIGS. 1 and 2 is omitted, the syringe being utilized with an alternative needle arrangement. In FIG. 13, a conventional double ended needle 28, is shown, the inner end of which replaces the needle 22.

FIG. 15 shows an arrangement in which the needle 28 may be single ended, an auxiliary hollow needle 35 being provided with a cylindrical sleeve 37 at the top which replaces the outer extremity of the inner portion of the coupling 27. A cap 39 is provided to retain the needle 35 within the coupling 27 until the needle 28 is fitted. When the syringe is to be used, the cap 39 is removed, and the sleeve of the needle is placed over the sleeve 37 and pushed down so that the needle 35 can penetrate the top of the vial and the needle 28 can be engaged with the coupling 27.

These needle arrangements are preferred for a syringe which is shipped in an essentially ready-to-use form, since the cap 2 may be pushed fully onto the cap 4 during assembly, yet the closure 60 remains unpenetrated until the needle (or other instrumentality as discussed below) is fitted at the time of use. On the other hand, the integral needle 22 is convenient where the assembly is to be utilized in the manner shown in FIGS. 11 and 12 and a capsule 12 is utilized. The inner surface of the cap 2 is provided with longitudinal ribs 23 which indent the soft aluminum of which the cap 4 is typically fabricated, and help retain the cap 2. The portions 41 and 43 of the cap 4, if present, are of course broken away prior to application of the cap 2.

The cap 4, closure 60, vial body 6 and piston 8 have already been described in detail above. The plunger 10 differs from that shown in FIGS. 1 and 2 in two respects. Its internal threads 20 end abruptly at abutments short of the front end of the plunger, so that when the plunger is screwed onto the extension of the piston, the ends of the threads meet adjustments at the abutments at the ends of the external grooves on the extension, which grooves in this embodiment stop short of the inner end of the extension, just before the inner end of the plunger contacts the rear surface of the piston. This prevents the plunger being screwed excessively tightly against the back of the piston in a manner which might result in rocking movements of the plunger being transmitted directly to the piston. Instead such movements are largely absorbed by the flexibility of the extension 18. Secondly, the flange 26 at the rear end of the plunger is moulded so that about one half of its periphery is separated into an integral loop 11, which can be flexed rearwardly about hinge lines 13, and serves either as a thumb loop to assist manipulation of the syringe, or a suspension loop from which the syringe can be hung during infusion of its contents as discussed further below. The synthetic plastic material from which the plunger is moulded is selected from those having hinge forming capability such as many pharmaceutically acceptable grades of polypropylene.

In order to provide further stabilization of the plunger, to prevent its withdrawal from the body, and to provide a finger grip during manipulation of the syringe, particularly where longer vial bodies 6 are utilized, an optional plunger stabilizer and adapter ring 15 may be provided. This has axially extending inner flanges 150 which enter the inner end of the body, and retaining lugs 152, which snap over the bead 7. Openings 154 and flanges 156 may be provided on the rear surface of the ring, as required, to assist in adapting the syringe to infuser apparatus such as that shown in FIG. 8.

Where the contents of the vial are liquid and do not require reconstitution or dilution, or reconstitution is effected by a diluent or solvent introduced via a needle or cannula through the closure 60, the cartridge cap 12 and diluent cartridge 14 are not required, the components already described constituting a complete syringe system. Otherwise these components may be provided and utilized as already described in relation to the embodiments of FIGS. 1 to 6 or FIGS. 11 and 12. The components themselves are however somewhat modified as shown in FIG. 14, to facilitate handling. A skirt portion 120 of the cap is formed with longitudinal slots 122 extending from its rear edge, and inner lips 124 around the inner periphery of that edge, whilst a front extension of the cartridge 14 is provided with ribs 142 extending longitudinally between the peripheral ridges 36 and 38, which ribs are accommodated by the slots 22. The ribs 142 are continued beyond a peripheral groove behind the ridge 36. The threads 30 and the cap 12 are reduced to short ridges between certain of the slots 122. Because of the slots, the cap 12 is readily engaged over the ridge 38, but when the assembly is inserted into the interior of the plunger 10, the diameter of the cap relative to the internal chamber of the plunger 13 such that the lip 124 is pressed into the ring of shallow recesses defined between the ridges 36 and 38 and the ribs 142, thus ensuring that the threads 30 may be engaged with the threads 20 within the plunger by turning the capsule, and inhibiting accidental forward movement of the cartridge 14 into the cap 12. Further turning of the capsule drives the needle 44 forward into the bore 48 (see FIG. 14) and thence through a septum in the bore into a small diameter counterbore 46 through the head of the piston (similar to that shown in FIG. 2), a piston modified in this manner being utilized when a diluent cartridge is to be used. The cartridge can then be forced forward so that the lips 124 ride over the ridge 38, permitting the needle 42 to penetrate the capsule whose contents can then be transferred to the vial by squeezing and/or aspiration.

Provided that the cap 12 is provided with a coupling 70, the capsule can of course also be utilized as described with reference to FIGS. 11 and 12, in which case the passage 46 in the piston is not required.

The capsule 14 is blow moulded from a heat sealable, film grade, low melting, high ethylene random propyleneethylene copolymer suitable for medical use. An example of such a material, already approved for pharmaceutical applications, is DYPRO (trade mark) polypropylene Z9350 from Fina Oil and Chemical Company which has a melting point of about 130° C. Such a material, formed by injection of ethylene into a propylene matrix, combines necessary qualities of transparency, impermeability and flexibility with the stability to withstand sterilizing temperatures in an autoclave, despite its low melting point; the pressure in the autoclave is maintained at a sufficient level to prevent bursting of the capsule during sterilization. Conventional capsule materials are unsuitable for use in this application, since they lack at least one of the necessary properties of flexibility, transparency, impermeability, penetrability, compatibility with conventional pharmaceutical diluents, and ability to withstand sterilization temperatures without failure or degradation.

Figure 16:
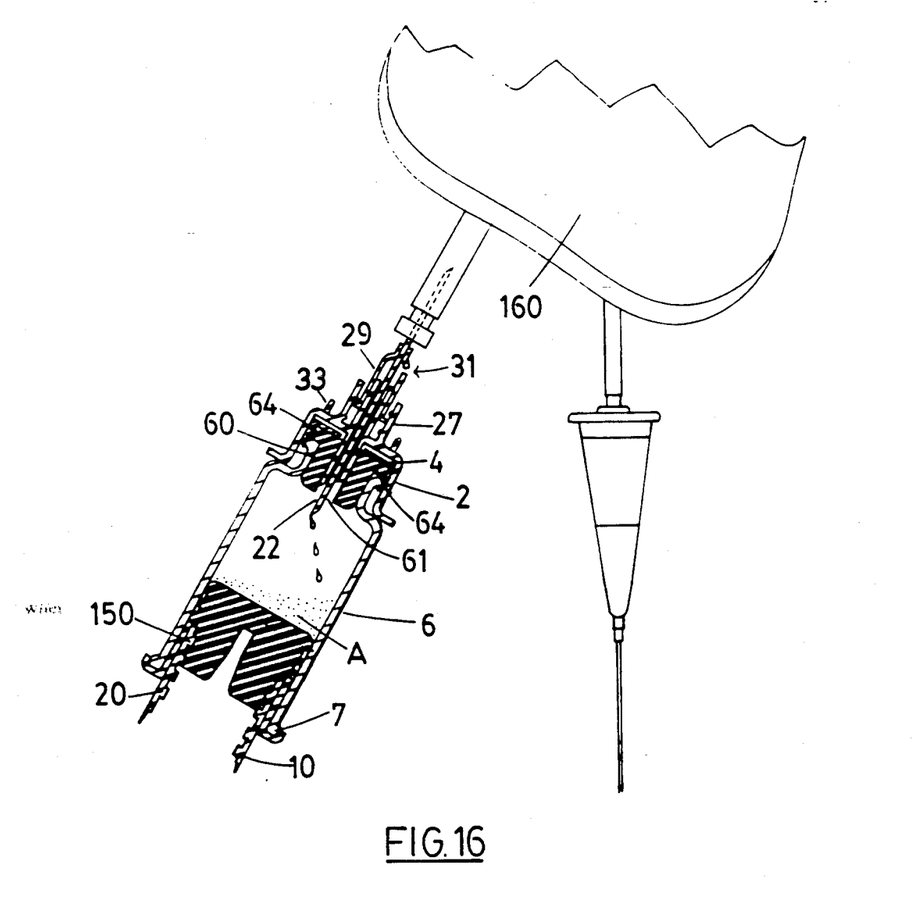
FIG. 16 is a fragmentary view of a syringe in accordance with the invention utilized in conjunction with an I.V. bag.

Utilization of syringes incorporating the above described modifications is similar to that of the other embodiments already described. The contents of the syringe may be delivered as already described with reference to FIGS. 6, 7 or 8, or in other ways. With a small modification to certain of the syringe components, the syringe contents may be reconstituted or diluted with fluid from an I.V. bag or minibag 160 and then injected into the bag for delivery, as shown in FIG. 16. Both the inner and outer components of coupling adaptor 27 of the cap 2 are elongated, and the bores of the inner component of the coupling adaptor and of the needle 22 are sufficient to provide an air venting passage around the read end of the needle 22 when fitted to the adaptor 27. A locking sleeve 29 on the needle 22, which sleeve engages the adaptor 27, is provided with a ventilation opening 31, such that when the sleeve 29 is screwed partially onto the adaptor as shown, air can escape through the sleeve as fluid from the bag 160 enters the syringe through the needle 22. When a desired amount of fluid has entered the syringe, the ventilation opening is closed by screwing the needle further onto the adaptor, following which the contents of the syringe may be injected into the bag 160.

The syringe of the invention is of course compatible with other syringe based drug administration systems.

I claim:

1. A vial formed of rigid transparent material and consisting of a cylindrical body, said body having an open bottom end having an external diameter at most only slightly greater than that of the remainder of the body, but sufficient relative to the height and center of gravity of the vial as a whole to support the latter in a stable manner when conveyed standing on its open end through vial filling and capping machinery, injectable material within the body, comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlapping the closure to secure the closure to the neck with the closure presenting a needle penetrable central portion, an impervious substantially solid piston of resilient material sealingly received within said body at its lower end beneath said injectable material and above said open bottom end, and a flexible reduced diameter extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap, wherein the piston and its extension are formed of rubber of at least 50 durometer hardness, and the extension is formed with a central bore to increase its flexibility.

2. A vial according to claim 1, wherein the piston is formed with multiple axially spaced peripheral ribs in compressive engagement with an inside cylindrical wall of the vial body.

3. A syringe comprising a vial according to claim 1, an outer cap which is a push fit over the cap of the vial and incorporates a needle mounting adaptor concentric with said needle penetrable portion of the closure, and a tubular cylindrical syringe plunger for coupling to said flexible extension of the piston.

4. A syringe according to claim 3, further including an inwardly directed hollow needle received within the needle mounting adaptor, and a sleeve secured to an outer end of the needle projecting beyond the adaptor such that pressure on the sleeve when an injection needle is coupled to the adapter will force the hollow needle through the needle penetrable portion of the closure of a vial to which the outer cap is applied.

5. A vial formed of rigid transparent material and consisting of a cylindrical body, said body having an open bottom end having an external diameter at most only slightly greater than that of the remainder of the body, but sufficient relative to the height and center of gravity of the vial as a whole to support the latter in a stable manner when conveyed standing on its open end through vial filling and capping machinery, injectable material within the body, a comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlaying the closure to secure the closure to the neck with the closure presenting a needle penetrable central portion, an impervious substantially solid piston or resilient material sealingly received within said body at its lower end beneath said injectable material and above said open bottom end, and a flexible reduced diameter extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap; wherein the extension is formed with external screw threads for engagement with complementary threads on the plunger, and with abutment means to limit the distance through which the plunger can be screwed onto said threads, such as to prevent rigid abutment of the plunger against the piston and to enable the extension to form a flexible connection between the plunger and the piston.

6. A vial formed of rigid transparent material and consisting of a cylindrical body, said body having an open bottom end terminating in a peripheral bead having an external diameter at most only slightly greater than that of the remainder of the body, but sufficient relative to the height and center of gravity of the vial as a whole to support the latter in a stable manner when conveyed freestanding on said bead through vial filling and capping machinery, injectable material within the body, a comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlaying the closure to secure the closure to the neck with the closure presenting a needle penetrable central portion, an impervious substantially solid piston of resilient material sealingly received within said body at its lower end beneath said injectable material and above said bead, and a flexible reduced diameter extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap, wherein the weight of the piston and its extension is at least a major portion of that of the vial body, and the height of the vial body does not exceed about 2.5 times the external diameter of the bead.

7. A vial formed of rigid transparent material and consisting of a cylindrical body, said body having an open bottom end having an external diameter at most only slightly greater than that of the remainder of the body, but sufficient relative to the height and center of gravity of the vial as a whole to support the latter in a stable manner when conveyed standing on its open end through vial filling and capping machinery, injectable material within the body, a comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlaying the closure to secure the closure to the neck with the closure presenting a needle penetrable central portion, an impervious substantially solid piston of resilient material sealingly received within said body at its lower end beneath said injectable material and above said open bottom end, and a flexible reduced diameter extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap, wherein the closure substantially fills the neck of the body, and has a top flange overlying the neck and defines a central bore extending from the bottom of the closure to a point beneath said needle penetrable central portion, and wherein the closure further defines a cross bore extending from an outer wall of the closure beneath the flange to said central bore, whereby said cross bore and said central bore together constitute a vent from the interior of the vial when the closure is partially inserted in the neck of the vial body.

8. A syringe comprising:

A vial formed of rigid transparent material and consisting of a cylindrical body, said body having an open bottom end terminating in a peripheral bead having an external diameter at most only slightly greater than that of the remainder of the body, but sufficient relative to the height and center of gravity of the vial as a whole to support the latter in a stable manner when conveyed freestanding on said bead through vial filling and capping machinery, injectable material within the body, a comparatively wide neck at the top of the body through said injectable material is filled into the body, an external peripheral flange surrounding the neck, an elastomeric closure applied to the neck, a cylindrical cap clamped onto the flange of the neck and having an annular inward extending flange at a top end overlying the closure to secure the closure to the neck with the closure presenting a needle penetrable central portion, an impervious substantially solid piston of resilient material sealingly received within said body at its lower end beneath said injectable material and above said bead, and a flexible reduced diameter extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap;

an outer cap which is a push fit over the cap of the vial and incorporates a needle mounting adaptor concentric with said needle penetrable portion of the closure; and a syringe plunger for coupling to said flexible extension of the piston, wherein a tubular cylindrical front end of the syringe plunger is press fitted onto a front end of the outer cap to form a separately sterilized subassembly.

9. A syringe, comprising:

A vial formed of rigid transparent material and consisting of a cylindrical body, said body having an open bottom end terminating in a peripheral bead having an external diameter at most only slightly greater than that of the remainder of the body, but sufficient relative to the height and center of gravity of the vial as a whole to support the latter in a stable manner when conveyed freestanding on said bead through vial filling and capping machinery, injectable material within the body, a comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlaying the closure to secure the closure to the neck with the closure presenting a needle penetrable central portion, an impervious substantially solid piston of resilient material sealingly received within said body at its lower end beneath said injectable material and above said bead, and a flexible reduced diameter extension integral with said piston, projecting downwardly from said piston but wholly within the body, for establishing a flexible connection to a syringe plunger in a zone between the piston and said open end of the body, whereby said vial may be converted into a syringe for ejection of the injectable material on movement of the piston towards the neck, by connection of said syringe plunger to said extension and connection of fluid conduit coupling means to said cylindrical cap;

an outer cap which is push fit over the cap of the vial and incorporates a needle mounting adaptor concentric with said needle penetrable portion of the closure; and a syringe plunger having a tubular cylindrical end portion for coupling to said flexible extension of the piston;

wherein a piston stabilizer ring is a snap fit on the bead, the piston stabilizer ring having flanges extending into the vial body between the inner wall of the body and the plunger to limit tilting of the plunger and prevent withdrawal of the piston from the body.

10. A syringe comprising a vial formed of rigid transparent material and consisting of a cylindrical body, said body having an open bottom end having an external diameter at most only slightly greater than that of the remainder of the body, but sufficient relative to the height and center of gravity of the vial as a whole to support the latter in a stable manner when conveyed standing on its open end through vial filling and capping machinery, injectable material within the body, a comparatively wide neck at the top of the body through which said injectable material is filled into the body, an external peripheral flange surrounding the neck, an elastomeric closure applied to the neck, a cylindrical cap clamped onto the flange of the neck and having an annular inward extending flange at a top end overlaying the closure to secure the closure to the neck with the closure presenting a needle penetrable central portion, an impervious substantially solid piston of resilient material sealingly received within said body at its lower end beneath said injectable material and above said open bottom end, and an extension integral with said piston, projecting downwardly from said piston but wholly within the body, a needle mounting adaptor concentric with said needle penetrable portion of the closure, and an elongated syringe plunger for coupling to said flexible extension of the piston;

wherein the syringe plunger is moulded from synthetic plastic having hinge-forming capability, and has an outwardly extending flange at its rear end, a peripheral portion of this flange being separated form the remainder around about half of its circumference, and the ends of the separated portion being connected to the remainder by integrally formed hinges to form a loop which can be pulled rearwardly of the flange.

11. A syringe plunger comprising an elongated stem defining a cylindrical recess at one end moulded from synthetic plastic material having hinge-forming capability, a cylindrical rubber piston of greater diameter than the plunger, an axial extension at one end of the piston entering within and releasably engaged with said cylindrical recess at one end of the plunger, and an outwardly extending flange at the other end of the plunger, a peripheral portion of this flange being separated from the remainder around about half of its circumference, and the ends of the separated portion being connected to the remainder by integral hinge-forming bridges to form a loop which can be pulled rearwardly of the flange.

* * * * *